United States Patent [19]

Walsh

[11] 4,298,347

[45] Nov. 3, 1981

[54] $^{13}CO_2$ BREATH TEST

[75] Inventor: Fraser M. Walsh, Arlington, Mass.

[73] Assignee: Kor Incorporated, Cambridge, Mass.

[21] Appl. No.: 124,341

[22] Filed: Feb. 25, 1980

[51] Int. Cl.$^3$ .......................................... G01N 33/52
[52] U.S. Cl. ................................. 23/230 B; 23/232 R
[58] Field of Search ................ 23/230 B, 232 R, 901, 23/907; 422/88, 91; 252/408

[56]  References Cited

U.S. PATENT DOCUMENTS

| | | | |
|---|---|---|---|
| 3,208,827 | 9/1965 | Borkenstein | 23/232 R X |
| 3,725,701 | 4/1973 | Link | 250/343 |
| 3,837,807 | 9/1974 | Tarkkanen | 23/230 B X |
| 4,027,972 | 6/1977 | Davies | 250/343 X |

OTHER PUBLICATIONS

Hirano et al., Analytical Biochemistry 96, 64–69 (1979).
Volpin et al., "The Reactions of Organometallic Compounds with Carbon Dioxide", Institute of Organo-Element Compounds, Academy of Science of the USSR, Moscow, USSR, pp. 313–386.
Helge et al., Chemical Abstracts, vol. 90, 1979, No. 90: 37276d.

Primary Examiner—Arnold Turk
Attorney, Agent, or Firm—Kenway & Jenney

[57]  ABSTRACT

A method for the analysis of exhaled carbon dioxide for clinical diagnostic application which contains a mixture of $^{13}CO_2$ and $^{12}CO_2$ is disclosed. The method includes the use of a solution which absorbs the carbon dioxide from the exhaled air, reacts with the carbon dioxide to form a ketone and uses the height of the unique infrared spectral peaks in the carbonyl frequency range to quantitate the $^{13}CO_2$ and the $^{12}CO_2$ components of the exhaled air.

2 Claims, 2 Drawing Figures $^{12}$C-BENZOPHENONE $^{12}$C-BENZOPHENONE $^{13}$C-BENZOPHENONE

$^{13}CO_2$ BREATH TEST

BACKGROUND OF THE INVENTION

Ethical considerations indicate that the use of radio-labeled drugs should be stringently limited in pre-term or term infants, children and women in potential or actual child-bearing status. Stable isotopically labeled drugs can and have been used in infant studies of bile acid metabolism (Watkins et al., 1973, 1975), alanine and glucose fluxes (Bier et al., 1973) and amino acid metabolism (Curtius et al., 1972). However, the extent of these studies has been limited by the lack of a low-cost instrument for routine analysis, the low sample number through-put and the high labor costs of the only major analytical method: gas chromatography-mass spectroscopy (GC-MS).

Increased clinical applications have been demonstrated for the diagnostic potential of "breath tests" using both radio and stable labeled carbon in diabetes, hepatitis, liver cirrhosis and cystic fibrosis. For example, Helge et al. (1978) showed that diabetic children eliminate $^{13}CO_2$ in their breath at a rate significantly lower than do normal children. The breath test is thus a simple and useful non-invasive procedure for the study of a wide range of metabolism disorders; its general use with clinically preferred $^{13}C$-labeled compounds has, however, been limited because GC-MS has remained the only practical analytical method.

To find a substitute for GC-MS, some effort has been applied to the direct measurement $^{13}C$-labeled carbon dioxide in the presence of $^{12}C$-labeled carbon dioxide under both private and public funds (NIH-NO1-HR-3-3002). Andros Inc. made and patented a fluorescent source infrared gas analyzer in 1973 (U.S. Pat. No. 3,725,701); in 1975, Andros Inc. described (U.S. Pat. No. 4,027,972) a second method of analysis of the level of gaseous $^{13}C$ labeled carbon dioxide through the application of radiant energy to standards in combination with the unknown. Accuracy on the order of five parts per $10^5$ was reported; however, the cost of this system was approximately twice that of a suitable GC-MS. This approach is thus at a cost competitive disadvantage to GC-MS and probably does not reduce the sample through-put and labor requirements.

SUMMARY OF THE INVENTION

It has now been discovered that a solution containing a solvent and an organometallic compound which reacts with gaseous carbon dioxide will form a soluble carbonyl compound which has a unique and well separated infrared spectral peak for the $^{12}C$ and $^{13}C$ products in the carbonyl frequency. The height of these peaks may be used as an analytical measure of the level of exhaled $^{13}C$- and $^{12}C$-labeled carbon dioxide for clinical diagnostic purposes. Thus relatively low cost, high through-put infrared spectroscopic apparatus may now be used for analysis of mass-labeled $CO_2$ in exhaled air.

The organometallic compounds used in the present invention may be represented by the formula RM wherein R is an organic moiety which forms, by reaction with $CO_2$, a carbonyl compound having unique infrared $^{12}C$ and $^{13}C$ spectral bands in the carbonyl frequency range (2100-1400 CM) and M is a metal ion chosen to facilitate the reaction between the organic moiety and $CO_2$ and to provide a high degree of solubility in the particular solvent chosen.

Accordingly, it is an object of this invention to provide a method for analysis of mass-labeled carbon dioxide by infrared spectroscopy.

Other objects of the present invention will become apparent from the detailed description which follows.

DESCRIPTION OF THE PREFERRED EMBODIMENT

In the preferred embodiment the chemical cocktail of the invention is a low-cost solution of an organometallic compound which rapidly absorbs and reacts with gaseous carbon dioxide to form benzophenone—a compound which has well separated infrared absorption bands when labeled in the carbonyl position with $^{13}C$ or $^{12}C$. Exemplary of organometallic compounds, which in solution react with carbon dioxide to form benzophenone, are phenyl lithium and phenyl magnesium halides. M. I. Volpin and I. S. Kolomnikov, "The Reactions of Organometallic Compounds with Carbon Dioxide", Organomet. React. (1975) p. 320 and H. Gilman and P. R. VanEss, JACS, 55, 1258 (1933), the teachings of which are incorporated herein by reference, report that a 70% yield of benzophenone can be obtained by passing gaseous carbon dioxide through a phenyl lithium solution:

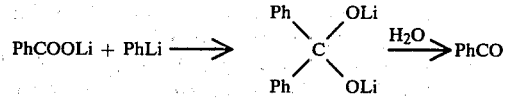

The cocktail preferably includes a solvating agent such as N,N,N',N'-tetramethylethylenediamine which serves to enhance the solubility of the organic metallic salt in the solvent although a solvating agent is not necessary to the practice of the present invention. The importance of the solubility of the organic metallic salt and of the organic product in the solvent is to provide a final solution with high concentrations of product so as to decrease the necessary level of sensitivity and accuracy of the analytical infrared spectrometer used to quantitate the levels of $^{13}C$- and $^{12}C$-labeled carbon dioxide in the exhaled air.

The concentration of the organometallic compound in solution and the relative amounts of cocktail and gaseous carbon dioxide are not in any way critical, but should be chosen in accordance with the sensitivity of the infrared analyzer and in keeping with the previously stated objective of providing a high concentration of the carbonyl product in the solution to be analyzed.

Figure 1:
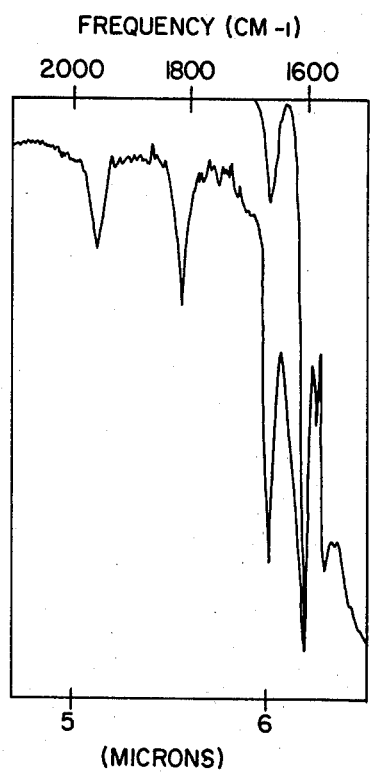
FIG. 1 is the infrared spectrum of $^{12}C$-benzophenone.
Figure 2:
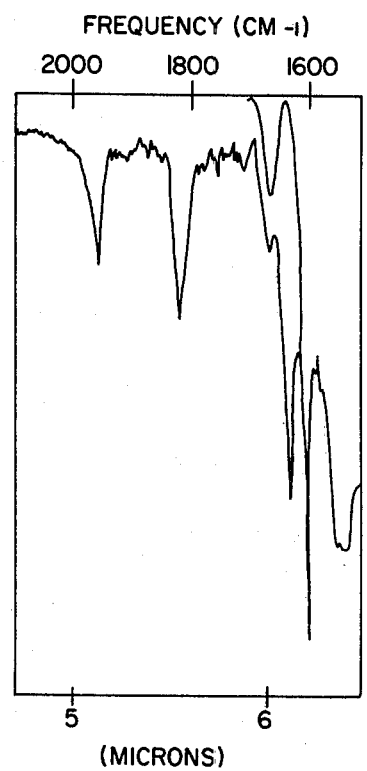
FIG. 2 is the infrared spectrum of $^{13}C$-benzophenone.

The carbonyl compound in solution, formed by bubbling (or otherwise contacting) the exhaled gas containing mass-labeled $CO_2$ through the solution of the organometallic compound, is then subjected to analysis by infrared spectroscopy. Infrared analysis in liquid phase is a technique with an inherent factor of a one thousand increase in sensitivity over gaseous phase analysis. The drawing shows the comparative infrared spectra over the region 2100-1500 cm$^{-1}$. In FIG. 1 the benzophenone carbonyl absorbance band is shown to be at approximately 1665 cm $-1$ for $^{12}$C-benzophenone and in FIG. 2 at 1630 cm $-1$ for $^{13}$C-benzophenone. The Table below shows the observed relationship between measured % transmittance (measured on a Perkin-Elmer Model 727 IR) and the mass ratio of $^{13}$CO$_2$ in the gas phase. Data recently published by Klein et al. (*Stable Isotopes,* ed. T. A. Baille, p. 3 University Park Press (1978) on the variance introduced into each step of $^{13}$CO$_2$ analysis in breath tests showed, based on GC-MS data from 39 analyses, the 95% confidence limit for a significant change in isotopic enrichment of breath test CO$_2$ to be 0.14% on a normal level of 1.1%. This change in enrichment concentration is approximately equal to a change in % transmittance of 0.07 based on the data provided in the Table below. This level of sensitivity is already available in a new instrument from Beckman Instruments Inc. (Model 600) with an advertised % transmittance sensitivity of 0.02%; this instrument uses multiscanning of the sample not Fourier analysis.

| Comparison of $^{13}$C$_2$/$^{12}$CO$_2$ Mass Ratio To Measured % Transmittance Ratio | |
|---|---|
| $^{13}$CO$_2$/$^{12}$CO$_2$ Ratio | % Transmittance Ratio |
| 13.7 | 9.3 |
| .67 | .67 |
| .59 | .54 |
| .47 | .42 |
| .01 | .01 |

For the purpose of clinical testing a patient is administered, by ingestion or injection, a $^{13}$C-labeled compound, for example glucose originating from corn starch which is naturally enriched with $^{13}$C. After a predetermined period of time the patient's breadth is analyzed as described above. Duchesne et al., *C. R. Acad. Sci. Ser. D.* (1973), 277 (20), pp. 2262-4, report studies on $^{13}$C/$^{12}$C isotope ratios in exhaled CO$_2$ wherein variance attributable to diabetes became apparent four hours after administration of $^{13}$C enriched glucose. Also see B. B. McIntier et al., *Proc. Semin. Use Stable Isotop. Clin. Pharmacol.* 1971 (Pub. 1972), 132-9.

EXAMPLE

A 700 ml sample of synthetic exhaled air containing 1% by weight $^{13}$CO$_2$ and 99% by weight $^{12}$CO$_2$ was allowed to equilibrate for two minutes at room temperature with two ml of a solution consisting of a 15-20% by weight solution of phenyllithium-N,N,N',N''-tetramethylethylenediamine in benzene. The organometallic compound (phenyl lithium) and the solvating agent (N,N,N',N''-tetramethylethylenediamine) were used on a molar ratio of 1:1. The solution was removed from contact from the gas, was allowed to set for one minute to permit physical settling of undesired solids, and then a sample (0.05 ml) of the benzene solution was placed between two standard salt (NaCl) plates and examined in a standard infrared spectrophotometer (Perking-Elmer Model 727). The height of the spectral peaks at $1665 \pm 2$ cm$^1$ ($^{12}$C-benzophenone) and at $1630 \pm 2$ cm$^{-1}$ ($^{13}$C-benzophenone) were measured and a ratio obtained. This ratio corresponded directly with the mass ratio of the two gases originally in the exhaled gas mixture.

What is claimed is:

1. A method for the analysis of mass-labeled carbon dioxide in exhaled air containing a mixture of $^{12}$CO$_2$ and $^{13}$CO$_2$ comprising:
   contacting a sample of the exhaled air with a solution of an organometallic compound that reacts with CO$_2$ to form $^{13}$C and $^{12}$C labeled carbonyl compounds having unique and well separated infrared spectral peaks for the $^{12}$C and $^{13}$C products and
   determining the relative amounts of the $^{13}$C and $^{12}$C carbonyl compound by infrared spectroscopy.

2. The method of claim 1 wherein said organometallic compound is selected from the group consisting of phenyl lithium and phenyl magnesium halides and said carbonyl compound is benzophenone.

* * * * *